(12) United States Patent
Taylor et al.

(10) Patent No.: US 7,700,131 B2
(45) Date of Patent: Apr. 20, 2010

(54) POWDERS HAVING CONTACT BIOCIDAL PROPERTIES

(75) Inventors: Alan Taylor, Chesterfield (GB); George Andrew Francis Roberts, Southwell (GB); Frances Ann Wood, Loughborough (GB)

(73) Assignee: Chitoproducts Limited (GB)

( * ) Notice: Subject to any disclaimer, the term of this patent is extended or adjusted under 35 U.S.C. 154(b) by 1307 days.

(21) Appl. No.: 11/183,726

(22) Filed: Jul. 18, 2005

(65) Prior Publication Data

US 2005/0250194 A1 Nov. 10, 2005

Related U.S. Application Data

(62) Division of application No. 10/289,676, filed on Nov. 7, 2002, now abandoned.

(30) Foreign Application Priority Data

Nov. 8, 2001 (GB) .................................. 0126866.3

(51) Int. Cl.
*A01N 59/16* (2006.01)
*A01N 25/12* (2006.01)
*A61K 33/38* (2006.01)
*A61K 31/28* (2006.01)
*A61K 9/14* (2006.01)

(52) U.S. Cl. ........................ 424/493; 424/488; 424/494; 424/495; 424/496; 424/618; 424/619; 514/54; 514/55; 514/495

(58) Field of Classification Search ................. 424/488, 424/618, 493, 494, 495, 496, 619; 514/54, 514/55, 495

See application file for complete search history.

(56) References Cited

U.S. PATENT DOCUMENTS

| 6,013,275 | A | 1/2000 | Konagaya et al. |
| 6,132,750 | A | 10/2000 | Perrier et al. |
| 6,231,848 | B1 | 5/2001 | Breitenbach et al. |
| 7,344,726 | B2 * | 3/2008 | Taylor et al. ................. 424/405 |
| 2002/0192298 | A1 | 12/2002 | Burrell et al. |

FOREIGN PATENT DOCUMENTS

| GB | 457783 | | 12/1936 |
| JP | 4122743 | A | 4/1992 |
| JP | 8268821 | A | 10/1996 |
| JP | 2000080233 | A | 3/2000 |
| RU | 2088234 | C1 | 8/1997 |
| RU | 2128047 | C1 | 3/1999 |
| RU | 2147237 | C1 | 4/2000 |
| WO | 00/49219 | * | 8/2000 |
| WO | WO 01/41774 | A1 | 6/2001 |

* cited by examiner

*Primary Examiner*—John Pak
(74) *Attorney, Agent, or Firm*—Peter S. Gilster; Greensfelder, Hemker & Gale, P.C.

(57) ABSTRACT

Powders having contact biocidal properties comprise a polysaccharide carrying atomic/metallic silver. The preferred polysaccharide is chitin, although other polysaccharides including chitosan, carboxymethyl celluloses and carrageenans can be used. The chitin may be obtained from deproteinated crustacean shells without demineralisation, thus being admixed with calcium carbonate and other naturally occurring minerals present in the shells, and may be enzyme deacetylated. The powders of the invention can be used as biocidal dusting powders, formulated into pastes, gels, hydrogels, creams, foams and aerosol sprays for pharmaceutical applications, or dissolved to form solutions for coating substrates such as skin, fabrics, glass, leather and paper to give a bactericidal surface. A particular application of such a solution is as a protective, post-wash treatment for workwear in a laundering process. The powders of the invention may be prepared by slurrying a polysaccharide, which is capable of interacting with silver ions and which is in powder form, in a liquid in which the polymer is insoluble, which liquid contains silver ions, filtering off the powder, washing the powder, reducing the silver ions which have interacted with the polysaccharide to atomic/metallic silver, and drying the powder. According to the polysaccharide chosen, the liquid is suitably water or aqueous ethanol. The silver ions may derive from silver nitrate. The reduction of the silver ions which have interacted with the polysaccharide to atomic/metallic silver can be effected photochemically through exposure to light. To hasten the reduction, however, the washed powder is preferably slurried in a solution of an alkali metal halide, irradiated under stirring with natural or artificial light containing an ultraviolet component, and again filtered off and washed, before drying it.

18 Claims, No Drawings

POWDERS HAVING CONTACT BIOCIDAL PROPERTIES

CROSS-REFERENCE TO RELATED APPLICATION AND CLAIM FOR PRIORITY

This application is a divisional of application Ser. No. 10/289,676, filed 7 Nov. 2002, now abandoned, entitled "Powders Having Contact Biocidal Properties", which application was based upon UK Patent Application No. 0126866.3 dated 8 Nov. 2001, entitled "Powders Having Contact Biocidal Properties", the contents of which are incorporated herein by reference in their entirety and continued preservation of which is requested.

FIELD OF THE INVENTION

The invention relates to powders having contact biocidal properties, to pastes, gels, hydrogels, creams, foams, aerosol sprays and other pharmaceutical application forms containing them, to solutions prepared from them, and to a process for their preparation.

BACKGROUND OF THE INVENTION

In our earlier International Patent Application No WO 02/15698, we described the preparation of articles having a contact biocidal property. A polymer solution which contains atomic/metallic silver in suspension or complexed with the polymer is applied to a substrate by impregnation or surface deposition and the article is dried. Alternatively the polymer solution contains a silver compound in solution, in suspension or complexed with the polymer instead of the atomic/metallic silver, and the silver compound is reduced to atomic/metallic silver after the application to the substrate. A second alternative is to convert the polymer solution to a fibre, film, powder or foam, effectively forming the article from the polymer solution instead of coating an existing article.

A disadvantage of the invention described in WO 02/15698 is the large liquor quantities resulting from the low solubility of the preferred polymer, chitosan. This can result in the use of an uneconomic quantity of silver. Also, transportation of solutions is expensive, and this may economically limit the applications of the prior invention.

SUMMARY OF THE INVENTION

The invention provides a powder having contact biocidal properties which comprises a polysaccharide carrying atomic/metallic silver.

The invention further comprises a method for the preparation of a powder having contact biocidal properties, the method comprising the steps of:
(a) slurrying a polysaccharide, which is capable of interacting with silver ions and which is in powder form, in a liquid in which the polysaccharide is insoluble, which liquid contains silver ions,
(b) filtering off the powder,
(c) washing the powder,
(d) reducing the silver ions which have interacted with the polysaccharide to atomic/metallic silver, and
(e) drying the powder.

DETAILED DESCRIPTION OF THE INVENTION

A powder having contact biocidal properties comprises a polysaccharide carrying atomic/metallic silver. A preferred polysaccharide for use in the invention is chitin. Chitin is a biopolymer found in crustacean exoskeletons (available as processing waste from the seafood industry). Current commercial extraction processes include a demineralisation treatment with hydrochloric acid to remove the calcium carbonate, also present in substantial quantities in the source material. This demineralisation generates high volumes of calcium chloride effluent which must be disposed of in an environmentally safe manner. It is therefore of interest that we have found it unnecessary to use demineralised chitin. Instead the deproteinated shells may be ground up and used without demineralisation. In this case the calcium carbonate and other mineral salts present act as natural bulking agents without any apparent loss in efficacy. Under these conditions there is also rapid formation of insoluble silver carbonate ($Ag_2CO_3$) on the surfaces of the particles. This product has high biocidal activity in its own right but it is preferable to add an alkali metal halide such as sodium chloride to allow rapid photochemical reduction to atomic/metallic silver.

Chitosan can be used in place of chitin. Chitosan is a polysaccharide, soluble in dilute acid, which can be obtained on a commercial scale by deacetylation of the biopolymer chitin in concentrated alkaline solutions at elevated temperatures. Chitosan contains many more amine groups and hence can adsorb a much higher concentration of silver ions.

Alternatively deacetylation of chitin particles, either demineralised or still containing the natural inorganic materials contained in the crustacean shell, may be carried out using enzymes. In this case the deacetylation will be limited to the surface of the particles since the enzymes are unable to penetrate the compact physical structure of chitin, effectively giving chitin particles with a chitosan coating. Treatment of such enzyme-deacetylated chitin particles with silver nitrate solution will result in a very high surface concentration of adsorbed silver ions but a much lower concentration in the interior. Since the biocidal effect of the silver containing powders, and hence the medical benefits, are due to contact by the bacteria or fungi with the particle surface, this results in a more efficient utilisation of the silver component.

Although chitin and chitosan are the polysaccharide materials of most interest in this invention, other polysaccharides containing groups capable of interacting with silver ions, either by electrostatic interactions or by formation of complexes, may be used in their place. Examples of these include carboxymethyl celluloses and carrageenans.

The powders of the invention may be prepared by slurrying a polysaccharide, which is capable of interacting with silver ions and which is in powder form, in a liquid in which the polysaccharide is insoluble, which liquid contains silver ions, filtering off the powder, washing the powder, reducing the silver ions which have interacted with the polysaccharide to atomic/metallic silver, and drying the powder.

The powder used in the method is preferably a fine powder having a particle size of less than 500 microns.

When using chitin or chitosan as the polymer, the liquid may be water. When using carboxymethyl celluloses, carrageenans or other water-soluble polymers, it is usually preferred to slurry the powder in an aqueous alcohol, for example aqueous ethanol, to prevent gelling or solubilisation during processing, although in some instances water will suffice.

The silver ions may derive from a silver compound dissolved in the slurry liquid. The silver compound is preferably silver nitrate, but any other soluble silver salt could be used.

Washing of the powder, after it has been filtered off, is intended to remove any excess silver ions, and may be effected with the same liquid as was used for slurrying (without, of course, the silver ion content). These intermediate filtration and washing steps may be omitted if all the silver ions have been adsorbed on the powder.

The silver ions will be photochemically reduced to metallic silver through exposure to light. This can, however, be accelerated by slurrying the washed powder with a solution of an alkali metal halide (preferably sodium chloride) and irradiating the slurry under stirring with natural or artificial light containing an ultraviolet component. The powder is then filtered off, washed and dried as before.

In these processes, it is desirable that the liquor ratio should be kept as low as possible given the constraints of the mechanical equipment used. Slurrying the polymer powder in a liquid should be construed broadly enough to include spraying the liquid on to the polysaccharide powder in an amount such as to produce a damp paste, which can be stood at ambient temperature in a sealed container to prevent evaporation.

The products may be used as contact biocidal dusting powders or made up into pastes, creams, gels, hydrogels, foams, aerosol sprays or other application forms typical for pharmaceutical applications. Additionally the powders may be dissolved in a solvent in which they are soluble, such as dilute acid for chitosan powders, and the resultant solutions used to coat a range of substrates, for example skin, fabrics, glass, leather, paper to give a bactericidal surface, or the solutions may be converted to solid foams or sponges by conventional techniques. When used in these forms they are more efficient than products prepared according to WO 02/15698. Much lower concentrations of silver are required for imparting effective bactericidal properties, as illustrated in Example 6 below. If the contact biocidal powders are intended for ultimate use in solution form, it is not necessary to use polymer powders as fine as sub-500 microns in their preparation.

One particular application for solutions prepared from the contact biocidal powders of the invention is as a bactericidal finish on workwear and fabrics for use where sterile conditions are important, such as in hospitals. Cross-infection, particularly with MRSA, is currently a major problem for many hospitals and the proven high activity of the contact biocidal powders of the invention against this organism suggests that its use in this situation would be highly beneficial. It is envisaged that the solutions would be used in a protective, post-wash treatment of the workwear in laundering processes.

The invention is illustrated by the following Examples.

Example 1

Chitin powder [10 g; particle size <500 µm] was slurried in 100 ml of distilled water. 0.25 g of silver nitrate dissolved in 10 ml distilled water was added and the mixture was stirred for 24 hours. The solids were filtered off, rinsed well in distilled water and then stirred for 2 hours in 100 ml of distilled water containing 1 g of sodium chloride. The solids were again filtered off, rinsed with distilled water and then stirred in suspension in distilled water (100 ml) while irradiated with daylight to convert $Ag^+$ to $Ag^\circ$. The chitin/silver complex was then isolated, dried and sieved to give a buff coloured powder having considerable biocidal activity.

Example 2

Chitosan powder [100 g; particle size <500 µm] was slurried in 1500 ml of distilled water. 6 g of silver nitrate dissolved in 20 ml distilled water was added and the mixture was stirred for 24 hours. The solids were filtered off and rinsed with distilled water. The filtrate showed no evidence of $Ag^+$ ions. The washed material was re-slurried in 1200 ml of distilled water and 2.1 g of sodium chloride dissolved in 10 ml distilled water was added. Stirring was continued in natural light for 64 hours after which the product was filtered off, washed with distilled water, dried at 70° C., and sieved to give a dark brown powder having considerable biocidal activity.

Example 3

Ball-milled deproteinated prawn shells still containing the calcium carbonate and other naturally occurring minerals [10 g; particle size <212 µm] was slurried in distilled water. The solids were filtered off, rinsed and re-suspended in distilled water. Silver nitrate solution [0.25 g in 10 ml distilled water] was added and the suspension stirred overnight. The solids were filtered off, rinsed and exposed to light for 24 hours while stirred in distilled water containing 1 g of sodium chloride. The grey powder was then isolated, rinsed and dried.

Example 4

Ball-milled deproteinated prawn shells still containing the calcium carbonate and other naturally occurring minerals [10 g; particle size <212 µm] was slurried in distilled water. The solids were filtered off, rinsed and re-suspended in distilled water. Silver nitrate solution [0.25 g in 10 ml distilled water] was added and the suspension stirred overnight. The solids were filtered off, and the grey powder rinsed and dried.

Example 5

5 g of carrageenan was slurried in ethanol:water (1:1 by volume) for 4 hours. The solids were then filtered off and suspended in fresh ethanol:water (4:1 by volume). There was then added under stirring 0.6 g of silver nitrate dissolved in distilled water to which an equal volume of ethanol had been added. Stirring was continued for 3 hours, at which stage the particles had taken on a pale reddish brown colour. The carrageenan was filtered off, rinsed in ethanol:water (1:1 by volume) to remove any free $Ag^+$ ions, and then steeped again in ethanol:water (1:1 by volume). 0.8 g of sodium chloride (dissolved in the minimum amount of distilled water to which an equal volume of ethanol had been added) was added. Rapid darkening of colour took place. The suspension was stirred for a further 40 hours to increase the extent of photochemical reduction. The product was filtered off, rinsed in ethanol: water (1:1 by volume), stirred in ethanol to dehydrate it and then dried at room temperature. The product was a grey-brown powder.

Example 6

5 g of the product obtained as described in Example 2 was dissolved in 500 ml of 0.1 M acetic acid. The brown solution obtained was used to treat a series of fabrics: a woven cotton fabric; a non-woven polyester fabric; a knitted carbon fibre fabric. The substrate was impregnated with the solution, squeezed in a pad mangle to remove surplus liquid and dried. The silver content varied from 0.04% on weight of fabric (o.w.f.) to 0.065% o.w.f. depending on the amount of solution picked up during padding. The samples were then evaluated using the Swiss SNV 195-920 test method for biocidal activity.

All samples showed a good inhibition effect at these levels of silver. For example the cotton fabric was rated Grade 2. In comparison, cotton treated by the process described in WO 02/15698 requires a silver concentration of at least 0.2% o.w.f. (a five-fold increase in silver content compared to the samples according to the invention) to give an equivalent rating in the Swiss SNV 195-920 test. This demonstrates the greater efficacy of the present process.

Example 7

2 g of the product obtained in Example 2 was dispersed in 100 ml of glycerol and 2 ml glacial acetic acid was added. After vigorous stirring the mixture formed a gelatinous paste.

Example 8

2 g of the product obtained in Example 2 was dispersed in 100 ml of glycerol and 3 ml lactic acid was added. After vigorous stirring the mixture formed a gelatinous paste.

Example 9

2 g of the product obtained in Example 2 was dissolved in 58 ml of distilled water containing 2 ml glacial acetic acid. Sorbitol (140 g) was dissolved in this solution to give a mixture which gelled on vigorous agitation.

Example 10

15 g of the product obtained in Example 1 was mixed with 4.25 g lanolin, 4.25 g hard paraffin, 4.25 g cetostearyl alcohol and 72.25 g white soft paraffin to produce a soft cream suitable for skin application.

Example 11

Powder samples prepared as described in Examples 1 to 5 were tested for their activity against MRSA and against *Dermatophilus congolensis*. The results are given in Tables 1 and 2 below.

TABLE 1

Biological activity: Tested against Methicillin resistant *Staphylococcus aureus* (MRSA NCTC 12493) by the Swiss SNV 195-920 test.

| Sample | Example No. | Grading | Average inhibition zone |
|---|---|---|---|
| Chitin/silver | 1 | 1 | 3.3 mm |
| Chitosan/silver | 2 | 1 | 6.3 mm |
| Chitin/minerals/silver | 3 | 1 | 2.3 mm |
| Chitin/minerals/silver | 4 | 1 | 3.4 mm |
| Carrageenan/silver | 5 | 1 | 1.7 mm |

TABLE 2

Biological activity: Tested against *Dermatophilus congolensis* (NCTC 5175: strain 11) by the Swiss SNV 195-920 test.

| Sample | Example No. | Grading | Average inhibition zone |
|---|---|---|---|
| Chitin/silver | 1 | 1 | 3.1 mm |
| Chitosan/silver | 2 | 1 | 6.5 mm |
| Chitin/minerals/silver | 3 | 1 | 4.0 mm |
| Chitin/minerals/silver carbonate | 4 | 1 | 2.7 mm |
| Carrageenan/silver | 5 | 1 | 2.4 mm |

What is claimed is:

1. A method for the preparation of a powder having contact biocidal properties, the method comprising the steps of:
   (a) slurrying a polysaccharide, which is capable of interacting with silver ions and which is in powder form, in a liquid in which the polysaccharide is insoluble, which liquid contains silver ions,
   (b) filtering off the powder,
   (c) washing the powder,
   (d) reducing the silver ions which have interacted with the polysaccharide to atomic/metallic silver, and
   (e) drying the powder.

2. A method for the preparation of a powder having contact biocidal properties, the method comprising the steps of:
   (a) slurrying a polysaccharide, which is capable of interacting with silver ions and which is in powder form and has a particle size of <500 microns, in a liquid in which the polysaccharide is insoluble, which liquid contains silver ions,
   (b) filtering off the powder,
   (c) washing the powder,
   (d) reducing the silver ions which have interacted with the polysaccharide to atomic/metallic silver, and
   (e) drying the powder.

3. A method according to claim 2 in which the polysaccharide is chitin.

4. A method according to claim 3 in which the chitin is obtained from deproteinated crustacean shells without demineralisation and is thus admixed with calcium carbonate and other naturally occurring minerals present in the shells.

5. A method according to claim 3 in which the chitin is enzyme deacetylated.

6. A method according to claim 4 in which the chitin is enzyme deacetylated.

7. A method according to claim 2 in which the polysaccharide is chitosan.

8. A method according to claim 2 in which the polysaccharide is a carboxymethyl cellulose.

9. A method according to claim 2 in which the polysaccharide is carrageenan.

10. A method for the preparation of a powder having contact biocidal properties, the method comprising the steps of:
    (a) slurrying a polysaccharide which is capable of interacting with silver ions and which is in powder form, in a liquid in which the polysaccharide is insoluble, which liquid contains silver ions,
    (b) filtering off the powder,
    (c) washing the powder,
    (d) reducing the silver ions which have interacted with the polysaccharide to atomic/metallic silver, and
    (e) drying the powder,
    wherein the liquid is water.

11. A method according to claim 10 in which the water contains silver nitrate.

12. A method according to claim 11 in which the washing of the powder is effected with de-ionised water to remove any excess silver ions.

13. A method according to claim 12 in which the washed powder is slurried in a solution of an alkali metal halide, irradiated under stirring with natural or artificial light containing an ultraviolet component in order photochemically to reduce the silver ions present to atomic/metallic silver, and again filtered off and washed, before drying it.

14. A method for the preparation of a powder having contact biocidal properties, the method comprising the steps of:
    (a) slurrying a polysaccharide which is capable of interacting with silver ions and which is in powder form, in a liquid in which the polysaccharide is insoluble, which liquid contains silver ions,
    (b) filtering off the powder, (c) washing the powder,
(d) reducing the silver ions which have interacted with the polysaccharide to atomic/metallic silver, and
(e) drying the powder,
wherein the liquid is aqueous ethanol.

15. A method according to claim 14 in which the aqueous ethanol contains silver nitrate.

16. A method according to claim 15 in which the washing of the powder is effected with aqueous alcohol to remove any excess silver ions.

17. A method according to claim 16 in which the washed powder is slurried in a solution of an alkali metal halide, irradiated under stirring with natural or artificial light containing an ultraviolet component in order photochemically to reduce the silver ions present to atomic/metallic silver, and again filtered off and washed, before drying it.

18. A method for the preparation of a powder having contact biocidal properties, the method comprising the steps of:

(a) slurrying a polysaccharide which is capable of interacting with silver ions and which is in powder form, in a liquid in which the polysaccharide is insoluble, which liquid contains silver ions,
(b) filtering off the powder,
(c) washing the powder,
(d) reducing the silver ions which have interacted with the polysaccharide to atomic/metallic silver, and
(e) drying the powder,
wherein the washed powder is slurried in a solution of an alkali metal halide, irradiated under stirring with natural or artificial light containing an ultraviolet component in order photochemically to reduce the silver ions present to atomic/metallic silver, and again filtered off and washed, before drying it.

* * * * *